US009895556B2

United States Patent
Bharat

(10) Patent No.: US 9,895,556 B2
(45) Date of Patent: Feb. 20, 2018

(54) MOTION-COMPENSATED DOSE RECEIVED BY TISSUE IN HIGH DOSE RATE BRACHYTHERAPY PROCEDURES

(71) Applicant: KONINKLIJKE PHILIPS N.V., Eindhoven (NL)

(72) Inventor: Shyam Bharat, Cortlandt Manor, NY (US)

(73) Assignee: Koninklijke Philips N.V., Eindhoven (NL)

(\*) Notice: Subject to any disclaimer, the term of this patent is extended or adjusted under 35 U.S.C. 154(b) by 392 days.

(21) Appl. No.: 14/413,561

(22) PCT Filed: Jul. 19, 2013

(86) PCT No.: PCT/IB2013/055955
§ 371 (c)(1),
(2) Date: Jan. 8, 2015

(87) PCT Pub. No.: WO2014/016749
PCT Pub. Date: Jan. 30, 2014

(65) Prior Publication Data
US 2015/0174431 A1 Jun. 25, 2015

Related U.S. Application Data

(60) Provisional application No. 61/675,455, filed on Jul. 25, 2012.

(51) Int. Cl.
*A61N 5/10* (2006.01)
(52) U.S. Cl.
CPC ......... *A61N 5/1071* (2013.01); *A61N 5/1001* (2013.01); *A61N 5/1007* (2013.01);
(Continued)

(58) Field of Classification Search
CPC .. A61N 5/1001; A61N 5/1064; A61N 5/1071; A61N 2005/1072;
(Continued)

(56) References Cited

U.S. PATENT DOCUMENTS 7,354,391 B2  4/2008  Stubbs
8,467,497 B2  6/2013  Lu et al.
(Continued)

OTHER PUBLICATIONS

Nag, S. et al. "Intraoperative planning and evaluation of permanent prostate brachytherapy: report of the american brachytherapy society", Int. J. Radiation Oncology Biol. Phys., vol. 51, No. 5, pp. 1422-1430, 2001.
(Continued)

*Primary Examiner* — Christine H Matthews
*Assistant Examiner* — Joshua D Lannu

(57) ABSTRACT

A system and method include a shape sensing enabled device (116) having at least one optical fiber (118). A source positioning module (124) is configured to receive optical signals from the at least one optical fiber within a structure and interpret the optical signals to provide motion information of treatment sources within the device. A dose determination module (130) is configured to provide one or more temporal bins representing a total treatment time. For each temporal bin, the dose determination module is configured to determine a dose received by a target area to be treated using the motion information of the treatment sources. The dose determination module is further configured to combine the dose received by the target area for each of the one or more temporal bins to determine a total dose received by the target area.

15 Claims, 3 Drawing Sheets

(52) U.S. Cl.
CPC ......... *A61N 5/1037* (2013.01); *A61N 5/1039* (2013.01); *A61N 5/1049* (2013.01); *A61N 5/1064* (2013.01); *A61N 2005/1055* (2013.01); *A61N 2005/1057* (2013.01); *A61N 2005/1058* (2013.01); *A61N 2005/1072* (2013.01); *A61N 2005/1074* (2013.01)

(58) Field of Classification Search
CPC .... A61N 2005/1057; A61N 2005/1074; A61N 5/1049; A61N 5/1039; A61N 5/1037; A61N 5/1007; A61N 2005/1058; A61N 2005/1055
See application file for complete search history.

(56) References Cited

U.S. PATENT DOCUMENTS

| | | | |
|---|---|---|---|
| 8,721,514 B2 | 5/2014 | Shechter | |
| 8,790,234 B2 | 7/2014 | Price | |
| 9,636,523 B2 | 5/2017 | Smith et al. | |
| 2009/0252291 A1 | 10/2009 | Weigno et al. | |
| 2010/0266099 A1 | 10/2010 | Busch et al. | |
| 2010/0312038 A1 | 12/2010 | Shechter | |
| 2012/0123187 A1 | 5/2012 | Van Der Laarse et al. | |
| 2013/0204072 A1* | 8/2013 | Verard | A61N 5/1027 600/8 |
| 2013/0303902 A1* | 11/2013 | Smith | A61B 6/12 600/431 |
| 2014/0088413 A1* | 3/2014 | Von Bucsh | A61B 5/0084 600/424 |

OTHER PUBLICATIONS

Bharat, S. et al. "Motion-compensated estimation of delivered dose during external beam radiation therapy: implementation in Philips' pinnacle (3) treatment planning system", Med Phys, Jan. 2012; 39(1):437-43.

* cited by examiner

MOTION-COMPENSATED DOSE RECEIVED BY TISSUE IN HIGH DOSE RATE BRACHYTHERAPY PROCEDURES

CROSS-REFERENCE TO PRIOR APPLICATIONS

This application is the U.S. National Phase application under 35 U.S.C. § 371 of International Application Serial No. PCT/IB2013/055955, filed on Jul. 19, 2013, which claims the benefit of U.S. Application Ser. No. 61/675,455, filed on Jul. 25, 2012. This application is hereby incorporated by reference herein.

This disclosure relates to estimating a dose received by a target area and more particularly to estimating a dose received by tissue using motion-compensation in medical applications.

High dose rate (HDR) brachytherapy involves the treatment of cancer through the temporary insertion of highly radioactive sources inside or in close proximity to a target site, such as the prostate. Prior to the first treatment session, multiple catheters are inserted transperineally into the target site. The catheters are delineated on transrectal ultrasound (TRUS) images and catheter position information is fed into a treatment planning system to determine optimal positions for HDR sources within each catheter and the time it spends at each position. The HDR brachytherapy treatment plan is then administered in a single fraction or in multiple fractions over the course of a few days. In some instances, computed tomography (CT) scans may be performed before and after each fraction to validate the positions of the catheters. However, while this affords some geometric validation of catheter positions during treatment, the dose that was actually delivered to the patient is not determined.

In accordance with the principles of the present invention, a system is provided which includes a shape sensing enabled device having at least one optical fiber. A source positioning module is configured to receive optical signals from the at least one optical fiber within a structure and interpret the optical signals to provide motion information of treatment sources within the device. A dose determination module is configured to provide one or more temporal bins representing a total treatment time. For each temporal bin, the dose determination module is configured to determine a dose received by a target area to be treated using the motion information of the treatment sources. The dose determination module is further configured to combine the dose received by the target area for each of the one or more temporal bins to determine a total dose received by the target area.

For example, the dose determination module can be configured to determine a dose delivered by the treatment sources using the motion information of the treatment sources. It is also possible that the dose determination module is configured to determine a dose delivered by the treatment sources using an initial treatment plan. Further, the dose determination module can be further configured to determine the dose received by the target area as the dose delivered by the treatment sources. The exemplary system can further also include an imaging module configured to provide motion information of the target area by imaging the target area. The dose determination module can be further configured to create probability distribution functions (PDFs) of motion patterns of each voxel of the target area based upon the motion information of the target area. It is also possible that the dose determination module be further configured to convolve the PDFs of each voxel with the dose delivered by the treatment sources to determine the dose received by the target area. The shape sensing enabled device can be a catheter. The imaging module can be configured to perform ultrasound and/or magnetic resonance imaging. The exemplary system can further include a planning module configured to modify a treatment plan based upon the motion information of the treatment sources and/or motion information of the target area. The total treatment time can include a time for a single fraction, multiple fractions, and/or fractions for a time period, for example.

Also, in accordance with the principles of the present invention, a workstation is provided which includes a shape sensing system including: a shape sensing enabled device having at least one optical fiber and a source positioning module configured to receive optical signals from the at least one optical fiber within a structure and interpret the optical signals to provide motion information of treatment sources within the device. A dose determination module is configured to provide one or more temporal bins representing a total treatment time. For each temporal bin, the dose determination module is configured to determine a dose received by a target area to be treated using the motion information of the treatment sources. The dose determination module is further configured to combine the dose received by the target area for each of the one or more temporal bins to determine a total dose received by the target area. A display can also be included.

For example, the dose determination module can be configured to determine a dose delivered by the treatment sources using the motion information of the treatment sources. It is also possible that the dose determination module is configured to determine a dose delivered by the treatment sources using an initial treatment plan. Further, the dose determination module can be further configured to determine the dose received by the target area as the dose delivered by the treatment sources. The exemplary workstation can also include an imaging module configured to provide motion information of the target area by imaging the target area. The dose determination module can be further configured to create probability distribution functions (PDFs) of motion patterns of each voxel of the target area based upon the motion information of the target area. It is also possible that the dose determination module is further configured to convolve the PDFs of each voxel with the dose delivered by the treatment sources to determine the dose received by the target area. The shape sensing enabled device can be a catheter. The imaging module can be configured to perform ultrasound and/or magnetic resonance imaging. The exemplary workstation can also include a planning module configured to modify a treatment plan based upon the motion information of the treatment sources and/or motion information of the target area. The total treatment time can include a time for a single fraction, multiple fractions, and/or fractions for a time period, for example.

Also, in accordance with the principles of the present invention, a method is provided which includes determining motion information of treatment sources within a shape sensing enabled device disposed within a structure. One or more temporal bins are provided representing a total treatment time. For each of the one or more temporal bins, a dose received by a target area to be treated is computed using the motion information of the treatment sources. The dose received by the target area for each of the one or more temporal bins is combined to determine a total dose received by the target area.

For example, the exemplary method can further include, for each of the temporal bin(s), computing a dose delivered by the treatment sources using the motion information of the treatment sources. It is also possible that exemplary method includes, for each of the temporal bin(s), computing a dose delivered by the treatment sources using an initial treatment plan. Computing the dose received by a target area can include determining the dose received by the target area as the dose delivered by the treatment sources. The exemplary method can also include imaging the target area to provide motion information of the target area. Further, the exemplary method can also include computing probability distribution functions (PDFs) of motion patterns of each voxel of the target area based upon the motion information of the target area. It is also possible for the exemplary method to further include convolving the PDFs of each voxel with the dose delivered by the treatment sources to determine the dose received by the target area. The shape sensing enabled device can be a catheter. Imaging the target area can include performing ultrasound and/or magnetic resonance imaging. Further still, the exemplary method can also include modifying a treatment plan based upon the motion information of the treatment sources and/or motion information of the target area. The total treatment time can include a time for a single fraction, multiple fractions, and/or all fractions, for example.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
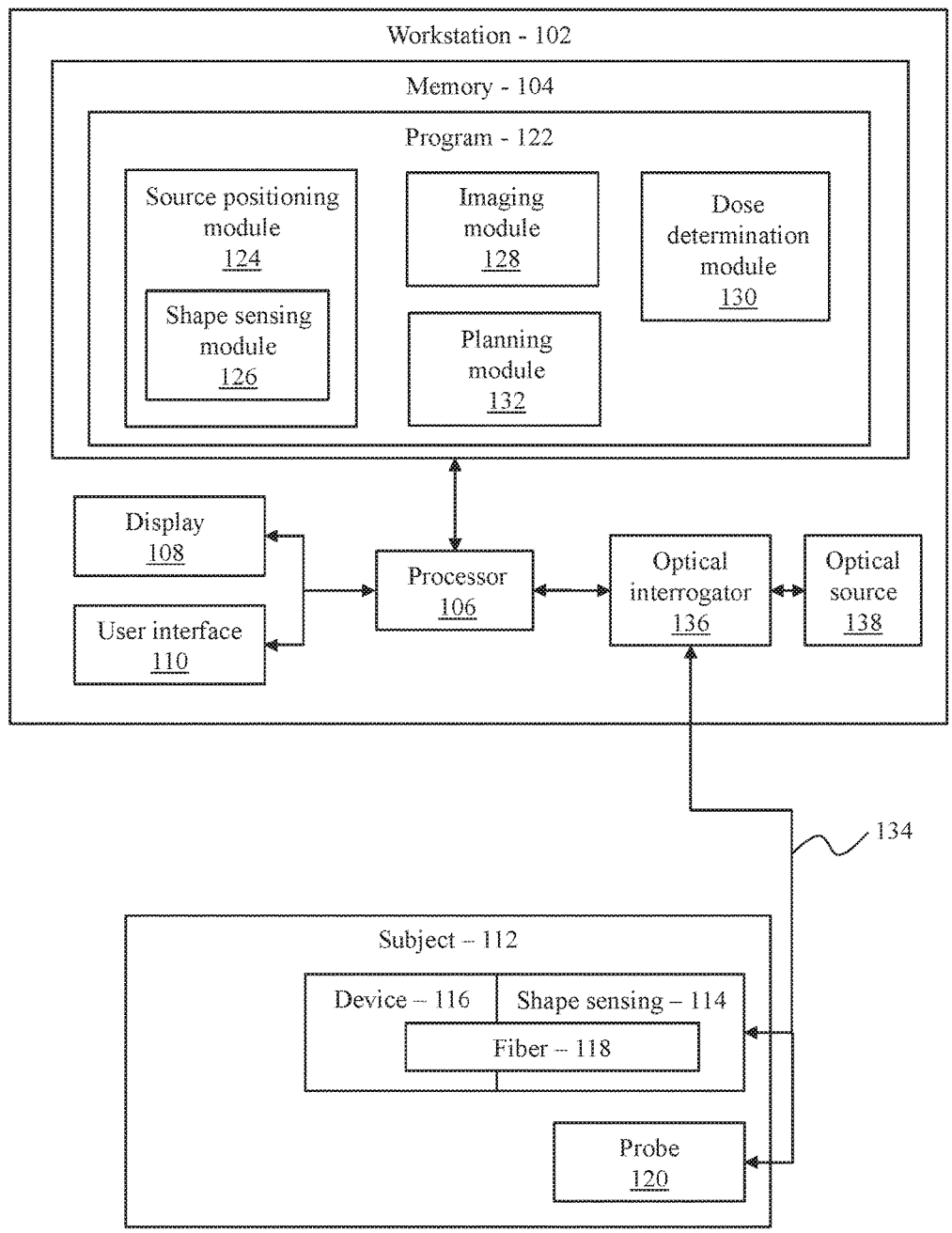
FIG. 1 is a block/flow diagram showing a system/method for determining a received dose in accordance with one embodiment.

In accordance with the present principles, a motion-compensated dose distribution received by a target area of a subject is provided. In particular, treatment time for, e.g., high dose rate (HDR) brachytherapy is represented with one or more temporal bins. For each bin, a 3D dose distribution delivered by radioactive sources within one or more catheters is determined based on motion of the sources. Preferably, shape sensing techniques are applied to determine a shape of the catheters. The position of the sources within the catheters may be determined by querying an afterloader device. A 3D dose distribution delivered by the sources is determined using the motion information of the catheters and sources and the initial treatment plan.

A 3D dose distribution received by a target area may then be determined based on motion information of the target area. In a preferred embodiment, motion information of the target area may be determined using imaging, such as, e.g., ultrasound. Probability distribution functions of motion patterns for each voxel of the target area may be computed. The probability distribution functions for each voxel may be convolved with the 3D dose distribution delivered by the sources to provide a 3D dose distribution received by the target area during that temporal bin. Where motion information of the target area is unavailable, such as where imaging is unable to be performed, the 3D dose distribution received by the target area is determined as the 3D dose distribution delivered by the sources. A total dose received by the target area may be determined by combining the 3D dose distribution received by the target area for each of the one or more temporal bins.

Advantageously, the dose received by the target area may be used for adaptive treatment planning, in accordance with one embodiment. For example, the dose received by the target area may be used to modify the treatment plan during delivery or between treatment fractions. In other embodiments, the dose received by the target area may be used to provide retrospective information for quality assurance of treatment delivery.

It also should be understood that the present invention will be described in terms of medical instruments and procedures; however, the teachings of the present invention are much broader and are applicable to the monitoring of any interventional procedure. In some embodiments, the present principles are employed in analyzing complex biological or mechanical systems. For example, the present principles may generally be applicable to the treatment monitoring of any interventional therapy procedure. In other embodiments, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a block diagram showing a system 100 for determining a received dose is illustratively depicted in accordance with one embodiment. The system 100 may include a workstation or console 102 from which procedures (e.g., HDR brachytherapy) are supervised and managed. Workstation 102 preferably includes one or more processors 106 and memory 104 for storing programs and applications. It should be understood that the functions and components of system 100 may be integrated into one or more workstations or systems.

Workstation 102 may include one or more displays 108 for viewing. The display 108 may also permit a user to interact with the workstation 102 and its components and functions. This is further facilitated by a user interface 110, which may include a keyboard, mouse, joystick, or any other peripheral or control to permit user interaction with the workstation 102.

Memory 104 may store a computer implemented program 122 including a source positioning module 124 configured to determine the motion of (e.g., radioactive) sources within one or more devices or instruments 116. The devices 116 preferably include a catheter, but may include one or more of a guidewire, a probe, an endoscope, a robot, an electrode, a filter device, a balloon device, or other component, etc. Catheters 116 may be placed within a subject 112 (e.g., patient) for treatment, such as high dose rate (HDR) brachytherapy. The present principles may also apply to other types of treatments and procedures.

Source positioning module 124 may employ a shape sensing system including shape sensing module 126 to accurately and continuously track the shape and pose associated with the catheter 116 and/or its surrounding region. The shape sensing system may include an optical interrogator 136 that provides selected signals and receives optical responses. An optical source 138 may be provided as part of the interrogator 136 or as a separate unit for providing light signals to the shape sensing device 114. Shape sensing device 114 includes one or more optical fibers 118 which may be coupled to the catheter 116 in a set pattern or patterns. Optical fibers 118 may be integrated into the catheter 116 or may be provided as a separate unit for providing light signals to the shape sensing device 114. The fibers 118 may be coupled to the workstation 102 through cabling 134. The cabling may include fiber optics, electrical connections, other instrumentation, etc. as needed. Shape sensing module 126 is configured to interpret optical feedback signals (and any other feedback, e.g., electromagnetic (EM) tracking) from a shape sensing device or system 114. Other methods of tracking the shape and pose of the catheter 116 are also contemplated.

Shape sensing 114 with fiber 118 may be implemented using any mechanism of optical fiber transmission/reflection. For example, shape sensing 114 with fiber 118 may be implementing using one or more of: wavelength-division multiplexed distributed sensing, time-wavelength-division multiplexed distributed sensing, interferometric detection, amplitude-based inherent scattering, etc. Preferably, shape sensing 114 with fiber 118 is based on the fiber Bragg grating (FBG) principle; however, other approaches are also contemplated, such as, e.g., Rayleigh scattering, Raman scattering or Brillouin scattering. FBG is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

The shape of the fibers 118 at any spatial location along its length is dependent on the internal strain developed in the fiber. The Bragg wavelength is sensitive to this strain. Shape sensing module 126 may use the strain in three or more FBGs (one in each fiber 118, in a group of three fibers 118) to calculate the local bend in the fiber group. Thus, the shape of the fiber is accumulated. A priori knowledge of the FBG positions along the fiber can be utilized to provide shape and position estimates of the fiber in the desired frame of reference.

The source positioning module 124 may also determine the position of the sources within the catheter 116 at any given point in time by, e.g., querying an afterloader device (not shown). The initial treatment plan may specify the dwell positions, which are the locations within the catheters 116 at which the sources are to be placed, and the dwell times, which are the amount of time at each location. The afterloader device is used to sequentially position the sources within the catheter 116. The source positioning module 124 may combine the positioning of the sources within the catheters 116 with the shape information of the catheter 116 determined by the shape sensing module 126 to provide motion information of the sources in a common frame of reference (e.g., in a transrectal ultrasound frame of reference).

The computer implemented program 122 may also include imaging module 128 configured to determine the shape and movement of the target area of the subject 112. The area of tissue for which the received dose is estimated may include organs at risk (OARs) in addition to the target area. Preferably, real-time three-dimensional (3D) transrectal ultrasound (TRUS) imaging may be implemented to gather 3D volumetric information of the target area. TRUS imaging may involve a two-dimensional or one-dimensional matrix array on a transrectal probe 120. The probe 120 may be mechanically or electronically steered. The probe 120 may connect to the workstation 102 through cabling 134. Other imaging techniques are also contemplated, such as, e.g., computed tomography (CT), magnetic resonance imaging (MRI), etc.

The computer implemented program 122 may include dose determination module 130 configured to determine an estimated 3D dose distribution received by the target area. Dose determination module 130 may combine the motion information determined by the source positioning module 124 and/or imaging module 128 with the initial treatment plan for, e.g., HDR brachytherapy to estimate the 3D dose distribution received by and/or delivered to the target area. The initial treatment plan may indicate dwell positions and dwell times of the sources within the catheters 116 implanted in a subject 112. Dose determination module 130 may preferably determine 3D dose plans using methods based on, e.g., the American Association of Physicists in Medicine (AAPM) Task Group (TG) Number 43 formalism for linear sources. Other methods of determining a 3D dose plan are also contemplated. The 3D dose distribution resulting from each source may be additively superimposed in the 3D dose plan to generate a cumulative 3D dose distribution.

Figure 2:
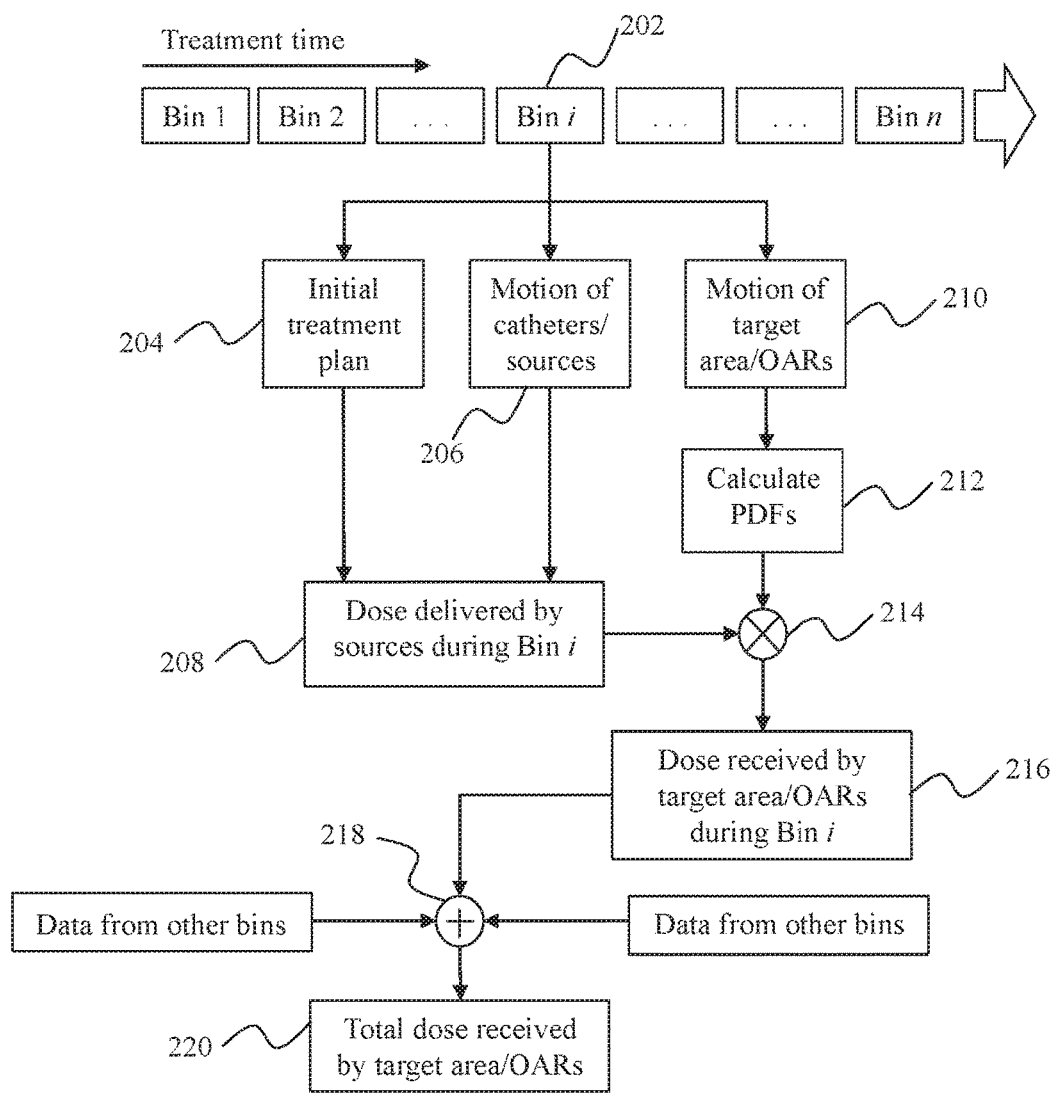
FIG. 2 is a block/flow diagram showing a system/method for determining a dose received by a target area using motion information in accordance with one embodiment.

In further detail, the dose determination module 130 may determine an estimation of the 3D dose received by the target area where information of the motion of the sources within the catheters 116 and information of the motion of the target area are available. Referring for a moment to FIG. 2, with continued reference to FIG. 1, a block/flow diagram 200 showing a determination of the dose received by a target area is illustratively depicted in accordance with one embodiment. The idea is to recompute the 3D dose distribution for smaller temporal bins and relate it to the positions of the target area and/or OARs at those respective times.

Multiple temporal bins, n, 202 are created which additively equal the entire treatment delivery time. The treatment delivery time may include the time for, e.g., an individual fraction, multiple fractions, fractions performed over a time period, all fractions to be performed, etc. Initially, the 3D dose distribution delivered by the sources is determined. For each bin 202, the motion information of the sources 206, determined by source positioning module 124, is combined with the initial treatment plan 204 to calculate a 3D dose distribution 208 delivered by the sources during that bin 202. Preferably, the 3D dose distribution delivered is determined using, e.g., AAPM TG 43. In one embodiment, the 3D dose distribution delivered is computed by using the dwell positions and dwell times of radioactive sources inside each catheter 116 and the known radioactive distribution pattern of each source to compute the overall dose delivered. In another embodiment, the (e.g., mathematical) relationship between source motion and the resulting impact on dose can be determined. Therefore, the delivered dose can be determined from the source motion patterns and the initial dose distribution, without having to re-compute the dose. Other embodiments for determining a 3D delivered dose distribution are also contemplated.

For each bin 202, motion information 210 of the target area, determined by the imaging module 128, may be used to determine a 3D dose distribution received by the target area. For each voxel of the target area of the subject 112, probability distribution functions (PDFs) 212 of the motion patterns are created. The PDF of each voxel represents the percentage of time spent by the voxel in that region of space. The percentages of each voxel add up to 100%. Each voxel's PDF is calculated by first quantifying the motion patterns of the target area. Motion patterns may include, e.g., translations and rotations from a given initial position. The motion patterns may be applied to each target voxel to calculate its PDF.

The PDFs for each voxel of the target area are convolved 214 with the static delivered 3D dose distribution for the entire target area to determine the dose received by that voxel in the presence of motion and, thus, the 3D dose distribution received during each bin 202. The cumulative 3D dose distribution 220 received by the target area over the entire treatment delivery time can be determined by additively 218 combining the 3D dose distributions received for each bin 202.

If motion information of the target area is not available due to technical limitations or other challenges that prevent the use of imaging techniques such as TRUS, the system 100 may still operate by assuming the target area to be static. Thus, for each bin 202, the delivered 3D dose distribution is assumed to be equivalent to the 3D dose distribution received by the target area. The total 3D dose distribution received by the target area over the entire treatment delivery time can be determined by additively combining the 3D dose distributions received during each bin 202.

The computer implemented program 122 may also include a planning module 132. The planning module 132 may involve one or more displays 108 and/or user interfaces 110. In one embodiment, the planning module 132 may provide real-time feedback to the clinician during treatment delivery. The planning module 132 may provide suggestions for modifications or automatic modifications to the treatment plan based on updated motion information of the sources and catheters 116 and the target area. For example, if the dose distribution received by the target area is less than the planned dose in the, e.g., posterior region of the target area, then the dwell positions and dwell times of the radioactive sources in the catheters 116 closest to the posterior region of the target area can be adjusted accordingly (e.g., increased) to compensate for the reduced dosage in that region.

In another embodiment, the planning module 132 may provide daily adaptive treatment planning. The planning module 132 may provide daily feedback in the form of a cumulative 3D dose delivered to the target area for all delivered fractions. The planning module 132 may provide suggestions for modifications or automatic modifications to the treatment plan for the remaining fractions.

In yet another embodiment, the planning module 132 may provide retrospective planning and delivery for quality assurance. The planning module 132 may provide retrospective estimates of a 3D dose distribution delivered to the target area for quality assurance purposes. A database may be built that relates the dosimetric outcomes to characteristics of patients. The characteristics of patients may include, for example, age, weight, disease type, disease stage, etc. Other characteristics are also contemplated.

Figure 3:
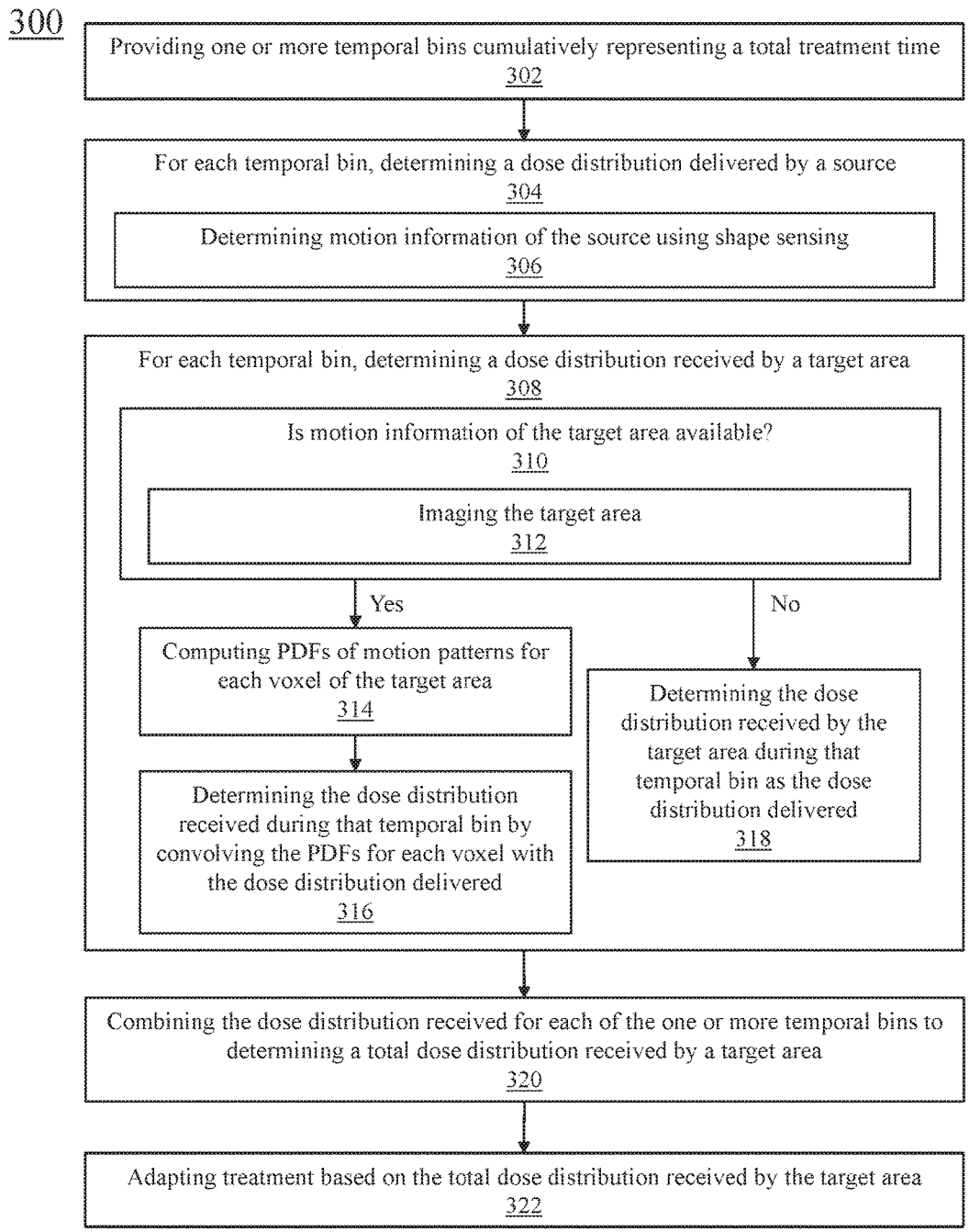
FIG. 3 is a block/flow diagram showing a system/method for determining a received dose in accordance with one embodiment.

Referring now to FIG. 3, a flow diagram showing a method 300 for estimating a dose received by a target area is illustratively depicted in accordance with one embodiment. In block 302, one or more temporal bins are created cumulatively representing a total treatment time. The total treatment time may represent, e.g., an individual fraction, multiple fractions, fractions performed over a time period, all fractions to be performed, etc. The idea is to recompute the 3D delivered dose distribution for smaller temporal bins and relate it to the positions of the target area at those times in order to compute the 3D dose distribution received by the target area. The area of tissue for which the received dose is estimated may include OARs in addition to the target area.

In block 304, for each temporal bin, a 3D dose distribution delivered by a (e.g., radioactive) source is determined. The source is preferably positioned within a device, such as a catheter; however, it is noted that the device may include one or more of a guidewire, a probe, an endoscope, a robot, an electrode, a filter device, a balloon device, or other medical component, etc. The catheter is positioned within a subject (e.g., patient) for treatment. In block 306, determining a dose distribution delivered by the source may include determining motion of the source. In a preferred embodiment, shape sensing may be employed to track the shape and pose of the catheter and/or its surrounding regions. Shape sensing may include interpreting feedback signals (e.g., optical, EM, etc.) from a shape sensing device. Other methods of determining motion of the source are also contemplated.

Shape sensing may include one or more optical fibers. The optical fibers may be integrated into the catheter or may be provided as a separate unit. Shape sensing may be implemented using any mechanism of optical fiber transmission/reflection. For example, shape sensing may be implementing using one or more of: wavelength-division multiplexed distributed sensing, time-wavelength-division multiplexed distributed sensing, interferometric detection, amplitude-based inherent scattering, etc. Preferably, shape sensing is based on the fiber optic Bragg grating (FBG) principle; however, other approaches are also contemplated, such as, e.g., Rayleigh scattering, Raman scattering or Brillouin scattering.

The shape of the fibers at any spatial location along its length is dependent on the internal strain developed in the fiber. Shape sensing may use the strain in three or more FBGs (one in each fiber, in a group of three fibers) to calculate the local bend in the fiber group. Thus, the shape of the fiber is accumulated. A priori knowledge of the FBG positions along the fiber can be utilized to provide shape and position estimates of the fiber in the desired frame of reference.

In one embodiment, determining a 3D dose distribution delivered by a source includes determining a position of the source within the catheter. An afterloader device may be queried to determine dwell positions for any given time. The shape of the catheter (e.g., using shape sensing) and the position of the source may be combined to provide the dose distribution delivered by the source. Preferably, the 3D dose distribution delivered is determined using, e.g., AAPM TG 43. In one embodiment, the 3D dose distribution delivered is computed by using the dwell positions and dwell times of radioactive sources inside each catheter and the known radioactive distribution pattern of each source to compute the overall dose delivered. In another embodiment, the (e.g., mathematical) relationship between source motion and the resulting impact on dose can be determined. Therefore, the delivered dose can be determined from the source motion patterns and the initial dose distribution, without having to re-compute the dose. Other embodiments for determining a 3D delivered dose distribution are also contemplated.

In block 308, for each temporal bin, a 3D dose distribution received by a target area is determined. In block 310, it is determined whether motion information of the target area is available. The motion information may preferably be obtained from imaging the target area, in block 312. Imaging the target area preferably includes real-time 3D TRUS. TRUS imaging may involve a two-dimensional or one-dimensional matrix array on a transrectal probe. The probe may be mechanically or electronically steered. Other imaging techniques are also contemplated, such as, e.g., CT, MRI, etc.

If motion information of the target area is available, in block 314, PDFs of motion patterns for each voxel of the target area are computed. In block 316, the 3D dose distribution received during that temporal bin is determined by convolving the PDFs for each voxel with the dose distribution delivered by the source. In block 318, if motion information of the target area is not available, the 3D dose distribution received by the target area during that temporal bin is determined to be the 3D dose distribution delivered for that temporal bin. Motion information may not be available due to, e.g., technical limitations or other challenges that may prevent the use of imaging. In block 320, a total dose distribution received by the target area is determined by combining the dose distribution received for each of the one or more temporal bins.

In block 322, treatment may be adapted based on the total dose distribution received by the target area. In one embodiment, on the fly real-time feedback may be provided to a clinician during treatment delivery. Suggestions for modifications or automatic modifications to the treatment plan may be provided based on updated motion information of the source and/or target area. For example, if the dose distribution received by the target area is less than the planned dose in the, e.g., posterior region of the target area, then the dwell positions and dwell times of the radioactive sources in the catheters closest to the posterior region of the target area can be adjusted accordingly (e.g., increased) to compensate for the reduced dosage in that region.

In another embodiment, daily adaptive treatment planning may be provided. For example, a cumulative 3D dose distribution delivered to the target area may be provided for all delivered fractions. Suggestions for modifications or automatic modifications to the treatment plan may be provided for the remaining fractions. In still another embodiment, a retrospective 3D dose distribution delivered by the sources and optionally, a retrospective 3D dose distribution received by the tissue may be provided for quality assurance purposes. A database may be built relating dosimetric outcomes to patient characteristics. Patient characteristics may include, for example, age, weight, disease type, disease stage, etc.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for motion-compensated dose received by tissue in high dose rate brachytherapy procedures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system, comprising:
  a shape sensing enabled device comprising at least one optical fiber;
  a source positioning module configured to receive optical signals from the at least one optical fiber and interpret the optical signals to provide motion information of the shape sensing enabled device, the motion information comprising a shape and a position of the shape sensing enabled device and a position of treatment sources within the shape sensing enabled device at any time during treatment; and
  a dose determination module configured to provide one or more temporal bins cumulatively equaling a total treatment time, wherein for each temporal bin, the dose determination module is configured to determine a dose received by a target area to be treated using the motion information of the shape sensing enabled device, the dose determination module further configured to combine the dose received by the target area for each of the one or more temporal bins to determine a total dose received by the target area.

2. The system as recited in claim 1, wherein the dose determination module is configured to determine a dose delivered by the treatment sources using the motion information of the treatment sources.

3. The system as recited in claim 1, wherein the dose determination module is configured to determine a dose delivered by the treatment sources using an initial treatment plan.

4. The system as recited in claim 2, wherein the dose determination module is further configured to determine the dose received by the target area as the dose delivered by the treatment sources.

5. The system as recited in claim 2, further comprising an imaging module configured to provide motion information of the target area by imaging the target area, wherein the imaging module is further configured to produce images comprising voxels.

6. The system as recited in claim 5, wherein the dose determination module is further configured to create probability distribution functions (PDFs) of motion patterns of each voxel of the target area based upon the motion information of the target area.

7. The system as recited in claim 6, wherein the dose determination module is further configured to convolve the PDFs of each voxel with the dose delivered by the treatment sources to determine the dose received by the target area.

8. The system as recited in claim 5, wherein the imaging module is configured to perform at least one of ultrasound or magnetic resonance imaging.

9. The system as recited in claim 1, wherein the shape sensing enabled device is a catheter.

10. The system as recited in claim 1, further comprising a planning module configured to modify a treatment plan based upon at least one of the motion information of the treatment sources or motion information of the target area.

11. The system as recited in claim 1, wherein the total treatment time includes a time for at least one of: a single fraction, multiple fractions, or fractions for a time period.

12. A workstation, comprising:
   a shape sensing system including:
      a shape sensing enabled device comprising at least one optical fiber;
      a source positioning module configured to receive optical signals from the at least one optical fiber and interpret the optical signals to provide motion information of the shape sensing enabled device, the motion information comprising a shape and a position of the shape sensing enabled device and a position of treatment sources within the shape sensing enabled device at any time during treatment;
   a dose determination module configured to provide one or more temporal bins cumulatively equaling a total treatment time, wherein for each temporal bin, the dose determination module is configured to determine a dose received by a target area to be treated using the motion information of the shape sensing enabled device, the dose determination module further configured to combine the dose received by the target area for each of the one or more temporal bins to determine a total dose received by the target area; and
   a display.

13. The workstation as recited in claim 12, wherein the dose determination module is configured to determine a dose delivered by the treatment sources using at least one of the motion information of the treatment sources or an initial treatment plan, and wherein the dose determination module is further configured to determine the dose received by the target area as the dose delivered by the treatment sources.

14. The workstation as recited in claim 13, further comprising an imaging module configured to provide motion information of the target area by imaging the target area, wherein the imaging module is further configured to produce images comprising voxels, wherein the dose determination module is further configured to create probability distribution functions (PDFs) of motion patterns of each voxel of the target area based upon the motion information of the target area, and wherein the dose determination module is further configured to convolve the PDFs of each voxel with the dose delivered by the treatment sources to determine the dose received by the target area.

15. A method, comprising:
   determining motion information of a shape sensing enabled device, the motion information comprising a shape and a position of the shape sensing enabled device and a position of treatment sources within the shape sensing enabled device at any time during treatment;
   providing one or more temporal bins cumulatively equaling a total treatment time;
   for each of the one or more temporal bins, computing a dose received by a target area to be treated using the motion information of the shape sensing enabled device; and
   combining the dose received by the target area for each of the one or more temporal bins to determine a total dose received by the target area.

* * * * *